(12) United States Patent
Lacour et al.

(10) Patent No.: US 6,627,649 B1
(45) Date of Patent: Sep. 30, 2003

(54) PHARMACEUTICAL COMPOSITIONS CONTAINING IN COMBINATION TWO ANTAGONISTS SELECTIVE OF ARGININE-VASSOPRESSIN V RECEPTORS, EVEN OF $V_{1A}$ AND $V_2$ RECEPTORS

(75) Inventors: Colette Lacour, Montpellier (FR); Dino Nisato, Saint Georges d'Orques (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/622,778

(22) PCT Filed: Mar. 1, 1999

(86) PCT No.: PCT/FR99/00450

§ 371 (c)(1),
(2), (4) Date: Oct. 6, 2000

(87) PCT Pub. No.: WO99/44613

PCT Pub. Date: Sep. 10, 1999

(30) Foreign Application Priority Data

Mar. 6, 1998 (FR) ............................................ 98 02874

(51) Int. Cl.$^7$ ............................................... A61K 31/40
(52) U.S. Cl. ...................................... 514/409; 514/414
(58) Field of Search .................................. 514/409, 414

(56) References Cited

U.S. PATENT DOCUMENTS

| | | | |
|---|---|---|---|
| 5,338,755 A | 8/1994 | Wagnon et al. | 514/414 |
| 5,618,833 A | 4/1997 | Foulon et al. | 514/409 |
| 5,994,350 A | 11/1999 | Foulon et al. | 514/232.8 |

FOREIGN PATENT DOCUMENTS

| | | |
|---|---|---|
| EP | 526 348 | 2/1993 |
| EP | 636 609 | 7/1994 |
| WO | WO97/15556 | 5/1997 |

OTHER PUBLICATIONS

Xu et al., Journal of Clinical Investigation, 1997; 99(4):1500–1505.*
Kinter et al., Journal of Cardiovascular Pharmacology, 1986;8(Suppl 7):S36–S43.*

* cited by examiner

*Primary Examiner*—Sreeni Padmanabhan
*Assistant Examiner*—Mojdeh Bahar
(74) *Attorney, Agent, or Firm*—Paul E. Dupont; Michael D. Alexander

(57) ABSTRACT

The invention relates to pharmaceutical compositions containing (2S)-1-{(2R,3S)-5-chloro-3-(2-chlorophenyl)-1-(3,4-dimethoxybenzenesulfonyl)-3-hydroxy-2,3-dihydro-1H-indole-2-carbonyl}pyrrolidine-2-carboxamide, a selective $V_{1a}$ arginine vasopressin receptor antagonist, in combination with the equatorial isomer of 1-{4-(N-tert-butylcarbamoyl)-2-methoxybenzenesulfonyl}-5-ethoxy-3-spiro{4-(2-morpholinoethyloxy)cyclohexane}indol-2-one or one of its salts, a selective $V_2$ arginine vasopressin receptor antagonist.

The invention relates to the use of such compositions for the production of medicines designed to treat all diseases for which either arginine vasopressin or the $V_2$ receptors are implicated or to treat all diseases related to a water overload.

14 Claims, No Drawings

PHARMACEUTICAL COMPOSITIONS CONTAINING IN COMBINATION TWO ANTAGONISTS SELECTIVE OF ARGININE-VASSOPRESSIN V RECEPTORS, EVEN OF $V_{1A}$ AND $V_2$ RECEPTORS

This is a national stage application of PCT/FR 99/00450, International filing date Mar. 1, 1999.

The object of the present invention is pharmaceutical compositions containing a combination of (2S)-1-{(2R,3S)-5-chloro-3-(2-chlorophenyl)-1-(3,4-dimethoxybenzenesulfonyl)-3-3-hydroxy-2,3-dihydro-1H-indole-2-carbonyl}pyrrolidine-2-carboxamide, a selective $V_{1a}$ arginine vasopressin receptor antagonist and the equatorial isomer of 1-{4-(N-tert-butyl-carbamoyl)-2-methoxybenzenesulfonyl}-5-ethoxy-3-spiro{4-(2-morpholinoethyloxy) cyclohexane}indol-2-one or one of its salts, a selective $V_2$ arginine vasopressin receptor antagonist and the use of such compositions for the production of medicines designed to treat all diseases in which either arginine vasopressin or the V2 receptors are implicated or to treat all diseases related to a water overload.

Vasopressin is a hormone known for its antidiuretic effect and its effect on the reOgulation of arterial blood pressure. It stimulates several types of receptors: $V_1$ ($V_{1a}$, $V_{1b}$ or $V_3$), $V_2$. These receptors are localized on the liver, blood vessels (coronary, renal, cerebral), platelets, kidney, uterus, adrenal, glands, central nervous system, hypophysis. The localization of the different receptors is described in: Jard, S. et al., "Vasopressin and oxytocin receptors: an overview" in Progress in Endocrinology, Imura H. and Shizume K., ed., Experta Medica, Amsterdam, 1988, 1183–1188, as well as in the following articles: Presse Médicale, 1987 16 (10) 481–485, J. Lab. Clin. Med., 1989, 114 (6) 617–632 and Pharmacol. Rev., 1991, 43 (1), 73–108. In particular, vasopressin exerts hormonal, cardiovascular, hepatic, renal, antidiuretic, aggregating effects and effects on the central and peripheral nervous systems, on the intestinal and uterine organs and on the pulmonary and ocular system.

The vasopressin receptor antagonists make it possible to inhibit the hormonal effects selectively. They may intervene in the regulation of the central and peripheral blood circulation, in particular the coronary, renal and gastric circulations, as well as on water balance and the release of the adrenocorticotrophic hormone (ACTH) (F. A. Laszlo et al., Pharmacol. Rev.,1991, 43, 73–108). Vasopressin itself as well as certain of its peptide analogues are used therapeutically and have shown their efficacy. Several reviews and many articles in the literature may be cited which demonstrate the potential therapeutic value of vasopressin receptor antagonists presently in clinical study: Vasopressin : P. Gross et al., ed. John Libbey Eurotext, 1993, in particular 243–257 and 549–562. F. A. Laszlo and F. A. Laszlo Jr., Clinical perspectives for vasopressin antagonists, Drug News Perspect., 1993, 6 (8); W. G. North, J. Clin. Endocrinol., 1991, 73, 1316–1320. J. J. Legros et al., Prog. Neuro-Pharmacol. Biol. Psychiat., 1988, 12, 571–586; K. E. Andersson et al., Drugs Today, 1988, 24, (7), 509–528; D. L. Stump et al., Drugs, 1990, 39, 38–53; S. Caltabiano et al., Drugs Future, 1988, 13, 25–30; Y. Mura et al., Clin. Nephrol. 1993, 40, 60–61; Faseb J., 1994, 8 (5), A 587:3398.

Furthermore, a recent review by J. D. Albright et al. (Current Pharmaceutical Design, 1997, 3, 615–632) reviews arginine vasopressin receptors and their antagonists and presents pharmacological studies and potential applications in human therapy. The $V_{1a}$ receptor antagonists are particularly to be recommended in diseases of the cardiovascular system. Moreover, the $V_2$ vasopressin receptor antagonists (also called "AVP-2 antagonists" or "$V_2$ antagonists") are particularly to be recommended in diseases of the cardiovascular system, the central and peripheral nervous system, the endocrine and hepatic system, the gastric and intestinal organs, the lungs and in ophthalmology. They act as potent aquaretics which act specifically on the renal resorption of water without leading to loss of electrolytes ($Na^+$, $K^+$) as do the diuretics traditionally used in the clinic such as furosemide or hydrochlorothiazide.

(2S)-1-{(2R,3S)-5-chloro-3-(2-chlorophenyl)-1-(3,4-dimethoxybenzenesulfonyl)-3-hydroxy-2,3-dihydro-1H-indole-2-carbonyl}pyrrolidine-2-carboxamide, the code name of which is SR 49059 of formula:

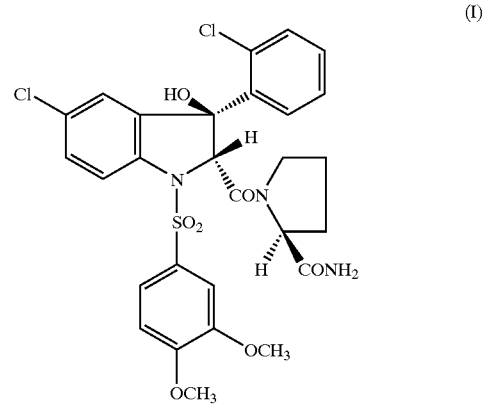

(I)

designated hereafter as compound A, has been described in the literature as being a potent and selective $V_{1a}$ arginine vasopressin receptor antagonist in various species, in particular towards human $V_{1a}$ receptors (C. Serradeil-Le Gal et al., J. Clin. Invest., 1993, 92 224–231). It possesses only a low affinity for the $V_2$ receptors. Compound A is the most potent antagonist selective for the human $V_{1a}$ receptors presently known.

The equatorial isomer of 1-{4-(N-tert-butylcarbamoyl)-2-methoxybenzenesulfonyl}-5-ethoxy-3-spiro{4-(2-morpholino-ethyloxy)cyclohexane}indol-2-one, the code name of which is SR 121463, or one of its salts of formula:

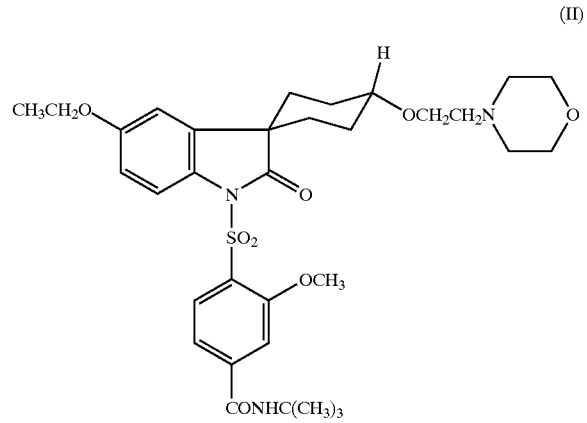

(II)

designated hereafter as compound B, has been described in the literature as being a potent and selective antagonist of $V_2$ arginine vasopressin receptor in various species, in particular towards human $V_2$ receptors (C. Serradeil-Le Gal et al., J. Clin. Invest., 1996, 98, 2729–2738). Compound B is the most potent antagonist selective for human $V_2$ receptors presently known.

It has now been found that the combination of compound A, a selective $V_{1a}$ arginine vasopressin receptor antagonist with compound B, a selective $V_2$ arginine vasopressin receptor antagonist, potentiates the effects produced by compound B used alone.

Thus the pharmaceutical compositions containing such a combination may be useful in particular for the treatment of diseases of the central and peripheral nervous system, the cardiovascular system, the endocrine and hepatic system, the renal domain, the gastric and intestinal domain, the pulmonary domain, oedematous states, hydroelectrolytic disorders, glaucoma, cataract and disorders of sexual behaviour in man and animals.

According to one of its features the object of the present invention is pharmaceutical compositions containing in combination:

(2S)-1-{(2R,3S)-5-chloro-3-(2-chlorophenyl)-1-(3,4-dimethoxybenzenesulfonyl)-3-hydroxy-2,3-dihydro-1H-indole-2-carbonyl}pyrrolidine-2-carboxamide (compound A), and the equatorial isomer of 1-{4-(N-tert-butylcarbamoyl)-2-methoxybenzenesulfonyl}-5-ethoxy-3-spiro{4-(2-morpholinoethyloxy)cyclohexane}indol-2-one (compound B) or one of its pharmaceutically acceptable salts, hydrates or solvates.

The salts of compound B are salts formed with classical pharmaceutically acceptable organic or mineral acids such as the hydrochloride, hydrobromide, sulfate, hydrogen sulfate, dihydrogen phosphate, methane sulfonate, maleate, fumarate, succinate, naphthalene-2-sulfonate, glyconate, gluconate, citrate, isethionate, benzenesulfonate, para toluenesulfonate.

The compounds A and B contained in the pharmaceutical compositions according to the invention are prepared according to known methods such as those described in EP-0 526 348 A or U.S. Pat No. 5 338 755 and WO 97/15 556, respectively.

The synergistic effect of the combination of compound A and compound B according to the invention has been demonstrated in particular by using the in vivo assay of water diuresis induced in the normally hydrated conscious rat according to the procedure described by C. Serradeil-Le Gal et al., J. Clin. Invest. 1996, 98, 2729–2738.

EXPERIMENTAL CONDITIONS

1) Experimental Protocol

The various assays are performed on Sprague Dawley male rats (280+/−20 g) obtained from Iffa Credo (France).

Twenty four hours before the start of the study, the rats were randomized and placed in metabolic cages with food and water ad libitum. They received orally 3 ml/kg of a 0.6% aqueous solution of methylcellulose. The urines were collected over a 24 hour period, i.e. day D-1.

The next morning the rats are treated orally (solvent or products alone or in combination) and returned individually to their metabolic cage for a period of 24 hours with food and water ad libitum. The urines are collected over a period of 24 hours after treatment, i.e. day D-0.

Urinary osmolality and the urinary excretion of $Na^+$ and $K^+$ ions are also measured during the 24 hour period before and after treatment. The urinary osmolality is measured with a freezing point depression osmometer (Fisk OS 110 model, Elvetec, Marseille, France) and the urinary concentrations of sodium and potassium are measured with a flame photometer (IL 943, Instruments Laboratories, Marseille, France).

The compounds alone (compound A, compound B) or in combination (compound A+compound B) are suspended in a 0.6% aqueous solution of methylcellulose and administered by gavage in a final volume of 3 ml/kg.

Compound B was used in the form of its dihydrogen phosphate monohydrate salt, the doses indicated are expressed in terms of the base.

2) Expression of the Results

The results are expressed in the form of the mean+/−SEM (standard error of the mean). The statistical analysis of the results is performed by means of a two factor variance analysis with repeated measurements of the time factor. The comparison of the means is made with the aid of the Dunnett test for a comparison with respect to a time or group of reference. Only the values of p lower than 5% are considered to be significant (p<0.05).

ASSAY No. 1: Comparative effect on urinary excretion, urinary osmolality and excretion of the $Na^+$ and $K^+$ ions in the rat after oral administration of compound A alone, compound B alone and of the combination compound A+ compound B.

a) Study Performed by Oral Administration of a Fixed Dose of Compound A (30 mg/kg) combined with increasing doses of compound B (0.3, 1 or 3 mg/kg).

The results obtained are presented in Table 1 (urinary volume), Table 2 (urinary osmolality) and Table 3 (urinary excretion of $Na^+$ and $K^+$ ions) below.

TABLE 1

| | | Urinary volume (ml) | |
|---|---|---|---|
| Group | mg/kg {ml/kg} | D-1 0–24 h | D-0 0–24 h |
| Control (1) solvent | {3} | 12.1 +/− 1.2 | 10.80 +/− 1.2 |
| Compound A (2) | 30 | 10.7 +/− 1.1 | 7.3 +/− 1.2 |
| Compound B (1) | 0.3 | 9.1 +/− 0.7 | 15 +/− 2 |
| | 1 | 9.1 +/− 0.7 | 25 +/− 2.2[a] |
| | 3 | 9.5 +/− 0.6 | 72.9 +/− 11.1[a] |
| Compound A + | 30 + 0.3 | 10.6 +/− 0.7 | 30.4 +/− 3.8[a] |
| (1) | 30 + 1 | 9.7 +/− 0.7 | 77.4 +/− 7.6[ab] |
| Compound B | 30 + 3 | 12 +/− 0.5 | 128.4 +/− 14.5[ab] |

[a] p < 0.05 versus control,
[b] p < 0.05 versus compound B
(1) n = 10 rats/group;
(2) n = 6 rats

TABLE 2

| | | Urinary osmolality (mOsmol/kg $H_2O$) | |
|---|---|---|---|
| Group | mg/kg {ml/kg} | D-1 0–24 h | D-0 0–24 h |
| Control (1) solvent | {3} | 1236 +/− 57 | 1675 +/− 132 |
| Compound A (2) | 30 | 1409 +/− 13 | 2462 +/− 379 |
| Compound B (1) | 0.3 | 1371 +/− 125 | 1075 +/− 165[a] |
| | 1 | 1376 +/− 99 | 618 +/− 27[a] |
| | 3 | 1443 +/− 46 | 292 +/− 40[a] |

TABLE 2-continued

| Group | mg/kg {ml/kg} | Urinary osmolality (mOsmol/kg H$_2$O) | |
|---|---|---|---|
| | | D-1 0–24 h | D-0 0–24 h |
| Compound A + (1) Compound B | 30 + 0.3 30 + 1 30 + 3 | 1238 +/− 66 1238 +/− 48 1169 +/− 51 | 642 +/− 54$^{ab}$ 269 +/− 24$^{ab}$ 173 +/− 27$^{ab}$ |

$^a$p < 0.05 versus control,
$^b$p < 0.05 versus compound B
(1) n = 10 rats/group;
(2) n = 6 rats

TABLE 3

| Group | mg/kg {ml/kg} | Na$^+$ (μmole) | | K$^+$ (μmole) | |
|---|---|---|---|---|---|
| | | D-1 0–24 H | D0 0–24 h | D-1 0–24 h | D0 0–24 h |
| Control (1) solvent | {3} | 1773 +/− 49 | 1728 +/− 127 | 2157 +/− 107 | 2367 +/− 112 |
| Compound A (2) | 30 | 1903 +/− 100 | 1668 +/− 131 | 2265 +/− 72 | 2190 +/− 182 |
| Compound B (1) | 0.3 | 1772 +/− 99 | 1668 +/− 201 | 2001 +/− 110 | 2254 +/− 200 |
| | 1 | 1840 +/− 123 | 1783 +/− 51 | 2034 +/− 68 | 2334 +/− 98 |
| | 3 | 1903 +/− 100 | 2168 +/− 197 | 2022 +/− 113 | 2648 +/− 230 |
| Compound A + (1) Compound B | 30 + 0.3 30 + 1 30 + 3 | 1847 +/− 101 1840 +/− 123 1904 +/− 100 | 2128 +/− 131 2368 +/− 130$^{ab}$ 2352 +/− 192$^a$ | 2258 +/− 115 2110 +/− 94 2330 +/− 60 | 2706 +/− 158 3010 +/− 204$^{ab}$ 2701 +/− 195 |

$^a$p < 0.05 versus control,
$^b$p < 0.05 versus compound B
(1) n = 10 rats/group;
(2) n = 6 rats The results show that:

compound A administered alone at the dose of 30 mg/kg does not modify the urinary excretion and the urinary osmolality in the rat over 24 hours. It also does not alter the urinary excretion of Na$^+$ and K$^+$ ions, the values obtained being comparable to those of the control group.

compound B administered alone at doses of 0.3, 1 or 3 mg/kg significantly increases the urinary excretion of the rat in a dose-dependent manner. It significantly diminishes urinary osmolality over 24 hours in a dose-dependent manner. It has no effect on the urinary excretion of Na$^+$ and K$^+$ ions.

the combination compound A+compound B significantly potentiates the increase of the urinary excretion obtained with compound B administered alone. It significantly potentiates the diminution of the urinary osmolality obtained with compound B administered alone. It has practically no effect on the urinary excretion of Na$^+$ and K$^+$ ions.

It has also been observed during this study that the combination of compound A with compound B, at the dose of 30+3 mg/kg, potentiates the prolongation of the duration of urinary excretion obtained with the compound B administered alone at the dose of 3 mg/kg.

b) Study Performed by Oral Administration of a Fixed Dose of Compound B (1 mg/kg) combined with increasing doses of compound A (3,10 or 30 mg/kg).

The results obtained are presented in Table 4 (urinary excretion), Table 5 (urinary osmolality) and Table 6 (urinary excretion of Na$^+$ and K$^+$ ions) below.

TABLE 4

| Group | mg/kg {ml/kg} | Urinary volume (ml) | |
|---|---|---|---|
| | | D-1 0–24 h | D0 0–24 h |
| Control (1) solvent | {3} | 12.1 +/− 1.2 | 10.80 +/− 1.2 |
| Compound A (2) | 30 | 10.7 +/− 1.1 | 7.3 +/− 1.2 |
| Compound B (1) | 1 | 11.7 +/− 1.5 | 31.6 +/− 3.5$^a$ |
| Compound A + (1) Compound B | 3 + 1 10 + 1 30 + 1 | 12.1 +/− 0.7 11.6 +/− 0.9 11.5 +/− 1.5 | 37 +/− 5.9$^a$ 47.7 +/− 4.2$^{ab}$ 69.4 +/− 3.5$^{ab}$ |

$^a$p < 0.05 versus control,
$^b$p < 0.05 versus compound B
(1) n = 10 rats/group;
(2) n = 6 rats

TABLE 5

| Group | mg/kg {ml/kg} | Urinary osmolality (mOsmol/kg H$_2$O) | |
|---|---|---|---|
| | | D-1 0–24 h | D0 0–24 h |
| Control (1) solvent | {3} | 1702 +/− 229 | 1988 +/− 271 |
| Compound A (2) | 30 | 1409 +/− 13 | 2462 +/− 379 |
| Compound B (2) | 1 | 1308 +/− 68 | 616 +/− 51$^a$ |
| Compound A + (1) Compound B | 3 + 1 10 + 1 30 + 1 | 1511 +/− 137 1570 +/− 67 1478 +/− 85 | 667 +/− 133$^a$ 429 +/− 35$^a$ 325 +/− 45$^a$ |

$^a$p < 0.05 versus control;
(1) n = 10 rats/group;
(2) n = 6 rats

TABLE 6

| Group | mg/kg {ml/kg} | Na$^+$ (μmole) | | K$^+$ (μmole) | |
|---|---|---|---|---|---|
| | | D-1 0–24 h | D0 0–24 h | D-1 0–24 h | D0 0–24 h |
| Control (1) solvent | {3} | 2249 +/− 94 | 2142 +/− 136 | 2464 +/− 99 | 2853 +/− 115 |
| Compound A (2) | 30 | 1903 +/− 100 | 1668 +/− 131 | 2265 +/− 72 | 2190 +/− 182 |
| Compound B (2) | 1 | 2039 +/− 80 | 2203 +/− 251 | 2519 +/− 65 | 2944 +/− 37 |
| Compound A + (1) Compound B | 3 + 1 10 + 1 30 + 1 | 2221 +/− 88 2248 +/− 103 2121 +/− 172 | 2359 +/− 160 2501 +/− 100 2475 +/− 204 | 2369 +/− 88 2432 +/− 103 2243 +/− 141 | 2924 +/− 147 3135 +/− 109 3184 +/− 407 |

(1) n = 10 rats/group;
(2) n = 6 rats

The results obtained show that:

compound B administered alone at the dose of 1 mg/kg significantly increases urinary excretion in the rat over 24 hours. It significantly diminishes the urinary osmolality of the rat and has no effect on the urinary excretion of Na$^+$ and K$^+$ ions.

the combination compound A+compound B significantly potentiates, in a dose-dependent manner, the increase in the urinary excretion obtained with compound B alone.

It potentiates in a dose-dependent manner the diminution of the urinary osmolality obtained with compound B administered alone. It has no effect on the urinary excretion of $Na^+$ and $K^+$ ions.

The results obtained in study a) and study b) show that the combination of compound A with compound B potentiates the aquaretic effect induced by compound B administered alone, without having an appreciable effect on the urinary excretion of $Na^+$ and $K^+$ ions. This potentiation of the aquaretic effect is found both in combining a fixed dose of compound A with variable doses of compound B and, conversely, in combining a fixed dose of compound B with variable doses of compound A.

For use as a medicine the pharmaceutical compositions containing the combination of compound A and compound B must be formulated in dosage units.

Thus, according to another feature, the present invention relates to pharmaceutical compositions containing:

(2S)-1-{(2R,3S)-5-chloro-3-(2-chlorophenyl)-1-(3,4-dimethoxybenzenesulfonyl)-3-hydroxy-2,3-dihydro-1H-indole-2-carbonyl}pyrrolidine-2-carboxamide (compound A); and the equatorial isomer of 1-{4-(N-tert-butylcarbamoyl)-2-methoxybenzenesulfonyl}-5-ethoxy-3-spiro{4-(2-morpholino-ethyloxy)cyclohexane}indol-2-one (compound B) or one of its pharmaceutically acceptable salts, hydrates or solvates;

in combination with at least one pharmaceutical excipient.

In the pharmaceutical compositions of the present invention for oral, sublingual, nasal, subcutaneous, intramuscular, intravenous, transdermal, topical or rectal administration, the active ingredients of the combination may be administered to man and animals in unit forms of administration mixed with standard pharmaceutical supports. The appropriate unit forms of administration include oral forms such as tablets, capsules, powders, granules and oral solutions or suspensions, sublingual and buccal forms of administration, aerosols, topical forms of administration, implants, subcutaneous, intramuscular, intravenous, intranasal or intraocular forms of administration and rectal forms of administration.

When a solid composition is prepared in the form of tablets, to the active ingredients of the combination, micronized or not, is added a pharmaceutical vehicle which may be composed of diluents like, for example, lactose, microcrystalline cellulose, starch and formulation adjuvants such as binders (polyvinylpyrrolidone, hydroxypropylmethylcellulose, etc . . . ), fluxes like silica and lubricants such as magnesium stearate, stearic acid, glycerol tribehenate, sodium stearylfumarate.

The tablets may be formed by means of different procedures, direct compression, dry granulation, wet granulation, hot melt.

Wetting agents or surfactants such as sodium lauryl sulfate may be added to the formulation.

The tablets may be coated (sucrose) or uncoated or coated with various polymers or other suitable materials.

The tablets may have a flash release or a delayed or sustained release resulting from the formation of polymeric matrices or the use of specific polymers for film formation.

A capsule preparation is obtained by simple mixing of the active ingredients with dry, liquid or semi-solid pharmaceutical vehicles (simple mixing or dry or wet granulation, hot melt).

The capsules may be hard or soft, film-coated or not so as to have a flash, sustained or delayed (enteric) activity.

A preparation in the form of a syrup or elixir may contain the active ingredients together with a sweetening agent, preferably calorie-free, methylparaben and propylparaben as antiseptic as well as an agent giving flavour and an appropriate colouring matter.

The powders or granules dispersible in water may contain the active ingredients in a mixture with dispersion agents, wetting agents or suspending agents like polyvinylpyrrolidone, as well as with sweetening agents or flavour correctors.

For rectal administration, recourse is had to suppositories which are prepared with binders melting at the rectal temperature, for example, cocoa butter or polyethyleneglycols.

For parenteral, intranasal or intraocular administration, aqueous suspensions, isotonic saline solutions or sterile and injectable solutions which contain pharmacologically compatible dispersion agents and/or solubilizing agents, for example propyleneglycol or butyleneglycol, are used.

Thus, in order to prepare an aqueous solution injectable intravenously a cosolvent is used such as, for example, an alcohol such as ethanol or a glycol such as polyethyleneglycol or propylene-glycol, and a hydrophilic surfactant such as Tween® 80. To prepare an oily solution injectable intramuscularly, the active ingredients may be solubilized by means of a triglyceride or a glycol ester.

For topical administration it is possible to use creams, ointments, gels, eye lotions.

For transdermal administration, it is possible to use multilaminated or reservoir-containing patches in which the active ingredients may be in alcoholic solution.

For administration by inhalation an aerosol is used which contains for example sorbitan trioleate or oleic acid as well as trichlorofluoromethane, dichlorofluoromethane, dichlorotetra-fluoroethane or any other biologically compatible propellant gas; it is also possible to use a system containing the active ingredients alone or combined with an excipient in the form of a powder.

The active ingredients may also be presented in the form of a complex with a cyclodextrin, for example, α, β, γ-cyclodextrin, 2-hydroxypropyl-β-cyclodextrin, methyl-β-cyclodextrin.

The active ingredients may also be formulated as microcapsules or microspheres, possibly with one or more supports or additives.

The sustained release forms useful in the case of chronic treatments may include the use of implants. These latter may be prepared in the form of oily suspensions or as suspensions of microspheres in an isotonic medium.

In each dosage unit the active ingredients of the combination are present in the quantities adapted to the intended daily doses. Generally, each dosage unit is suitably adjusted to the dosage and type of administration prescribed, for example, tablets, capsules and the like, sachets, vials, syrups and the like, drops so that such a dosage unit contains from 2.5 to 1000 mg, and preferably from 2.5 to 250 mg, of compound A and from 0.5 to 500 mg, and preferably from 1 to 250 mg, of compound B, said dosage unit requiring administration once to four times a day.

According to another feature, the present invention relates to the use of the pharmaceutical compositions containing in combination compound A with compound B for the preparation of medicines designed to treat all diseases in which either arginine vasopressin or the $V_2$ receptors are implicated or to treat all diseases related to a water overload.

According to another feature, the present invention relates to the use of the pharmaceutical compositions containing in combination compound A with compound B for the preparation of medicines designed to treat diseases of the central and peripheral nervous system, the cardiovascular system, the endocrine and hepatic system, renal domain, the gastric and intestinal domain, the pulmonary domain, oedematous states, hydroelectrolytic disorders, glaucoma, cataract and disorders of sexual behaviour in man and animals.

Thus, the pharmaceutical compositions according to the invention may be used in the treatment or prevention of various vasopressin-dependent diseases as well as in the dysfunction of vasopressin secretion, cardiovascular diseases like hypertension either in the general population or in particular ethnic groups, pulmonary hypertension, cardiac insufficiency, circulatory insufficiency, myocardial infarction, atherosclerosis or coronary vasospasm, in particular in smokers, unstable anginas and PTCA (percutaneous transluminal coronary angioplasty), cardiac ischemia, hemostatic disturbances, in particular hemophilia, the von Willebrand syndrome; diseases of the central nervous system, migraine, cerebral vasospasm, cerebral hemorrhage, cerebral ischemia, cerebral oedemas, depression, anxiety, bulimia, psychotic states, memory disorders, for example; renal dysfunctions like diabetic nephropathy, renal insufficiency, oedemas, renal vasospasm, necrosis of the renal cortex, nephrotic syndrome, hyponatremias, hypokalemia, diabetes or renal lithiasis; diseases of the gastric system, like gastric vasospasm, portal hypertension, hepatocirrhosis, ulcers, the pathology of vomitings, for example, nausea including nausea due to chemotherapy, travel sickness or also the syndrome of inappropriate secretion of the antidiuretic hormone (SIADH), the Schwartz-Bartter syndrome, the complications of sugar diabetes; diseases of the hepatic system such as liver cirrhoses; abdominal ascites and all the disorders causing abnormal water retention, either generalized or localized; cellulitis; adrenal disorders (Cushing's disease) and in particular hypercorticism and hyperaldosteronism. The compositions according to the invention may also be used in the treatment of disorders of sexual behaviour, in overweight or excess weight and obesity by replacing advantageously the standard diuretics already used for this indication. In women the compositions according to the invention may be used to treat dysmenorrhea or premature labour. The compositions according to the invention may also be used in the treatment of small cell lung cancers, hyponatremic encephalopathies, Raynaud's disease, Meniere's syndrome, pulmonary syndrome, glaucoma and the prevention of cataract and in post-operative treatments, in particular after abdominal, cardiac or hemorrhagic surgery.

Very especially, the pharmaceutical compositions according to the invention are useful for the production of a medicine to treat the diseases of the cardiovascular system, renal dysfunctions, hydroelectrolytic disorders, oedematous states, glaucoma and cataract.

More precisely, the pharmaceutical compositions according to the invention are useful for the production of a medicine to treat hydroelectrolytic disorders such as hyponatremia and oedematous states.

The compositions of the present invention may contain, besides the above combination of compound A with compound B or their pharmaceutically acceptable salts, solvates and hydrates, other active principles which may be used in the treatment of the disorders or diseases indicated above.

Thus, the object of the present invention is also pharmaceutical compositions containing a combination of several active ingredients, one of which is constituted by the combination of compound A with compound B according to the invention.

Thus, according to the present invention, it is possible to prepare pharmaceutical compositions containing the combination according to the invention associated with a compound acting on the renin-angiotensin system such as a converting enzyme inhibitor, an angiotensin II antagonist, a renin inhibitor. It is also possible to associate the combination according to the invention, for example, with a peripheral vasodilator, a calcium inhibitor, a beta blocker, an alpha-1-blocker or diuretic. Such compositions should be useful in particular in the treatment of hypertension or heart failure.

Advantageously, it is possible to prepare pharmaceutical compositions containing the combination of compound A with compound B according to the invention associated with a specific angiotensin II antagonist, preferably irbesartan.

These combinations will make it possible to reinforce the therapeutic activities of the combination according to the invention.

EXAMPLE 1

Capsule Dosed at 25 mg of Compound A and 2.5 mg of Compound B

| | |
|---|---|
| Micronized compound A | 25.00 mg |
| Compound B expressed as free base | 2.50 mg |
| Lactose monohydrate | 324.90 mg |
| Modified maize starch | 57.77 mg |
| Anhydrous colloidal silica | 2.125 mg |
| Magnesium stearate | 4.25 mg |
| Talc | 8.50 mg |
| For an opaque white capsule No. 0 filled to | 425 mg |

EXAMPLE 2

Capsule Dosed at 100 mg of Compound A and 10 mg of Compound B

| | |
|---|---|
| Micronized compound A | 100.00 mg |
| Compound B expressed as free base | 10.00 mg |
| Lactose monohydrate | 253.60 mg |
| Modified maize starch | 46.52 mg |
| Anhydrous colloidal silica | 2.125 mg |
| Magnesium stearate | 4.25 mg |
| Talc | 8.50 mg |
| For an opaque white capsule No. 0 filled to | 425 mg |

EXAMPLE 3

Tablet Dosed at 25 mg of Compound A and 2.5 mg of Compound B

| | |
|---|---|
| Micronized compound A | 25.00 mg |
| Compound B expressed as free base | 2.50 mg |
| Lactose monohydrate QSP | 300.00 mg |
| Maize starch | 50.00 mg |
| Polyvinylpyrrolidone K30 | 9.00 mg |
| Purified water QS | |
| Magnesium stearate | 3.00 mg |
| For an uncoated tablet finished at | 300 mg |

EXAMPLE 4

Tablet Dosed at 100 mg of Compound A and 10 mg of Compound B

| | |
|---|---|
| Micronized compound A | 100.00 mg |
| Compound B expressed as free base | 10.00 mg |
| Lactose monohydrate QSP | 450.00 mg |
| Microcrystalline cellulose 50 μm | 50.00 mg |
| Hydroxypropylmethylcellulose 6 CP | 13.50 mg |
| Purified water QS | |
| Magnesium stearate | 4.50 mg |
| Cross-linked sodium carboxymethylcellulose | 9.00 mg |
| For an uncoated tablet finished at | 450 mg |

What is claimed is:

1. A pharmaceutical composition containing in combination: a synergistically effective amount of (2S)-1-{(2R,3S)-5-chloro-3-(2-chlorophenyl)-1-(3,4-dimethoxybenzenesulfonyl)-3-hydroxy-2,3-dihydro-1H-indole-2-carbonyl}pyrrolidine-2-carboxamide (compound A) and a synergistically effective amount of the equatorial isomer of 1-{4-(N-tert-butylcarbamoyl)-2-methoxybenzenesulfonyl}-5-ethoxy-3-spiro{4-(2-morpholinoethyloxy)cyclohexane}indol-2-one (compound B), or one of its pharmaceutically acceptable salts, hydrates or solvates.

2. A pharmaceutical composition according to claim 1 in which the active ingredients of the combination are mixed with at least one pharmaceutical, excipient.

3. A pharmaceutical composition according to claim 2, in unit dosage form.

4. A pharmaceutical composition according to claim 3, containing from 2.5 to 1000 mg of compound A and from 0.5 to 500 mg of compound B.

5. A pharmaceutical composition according to claim 4, containing from 2.5 to 250 mg of compound A and from 1 to 250 mg of compound B.

6. A pharmaceutical composition according to claim 1 additionally containing in addition, another active ingredient.

7. A pharmaceutical composition according to claim 6, characterized in that the other active ingredient is a angiotensin II receptor antagonist.

8. A pharmaceutical composition according to claim 7, characterized in that the angiotensin II receptor antagonist is irbesartan.

9. A method for the treatment of hyponatremia or edematous states which comprises administering to a patient in need of such treatment a therapeutically effective amount of a composition according to claim 1.

10. A method for the treatment of hyponatremia or edematous states which comprises administering to a patient in need of such treatment a therapeutically effective amount of a composition according to claim 8.

11. A method according to claim 9 for the treatment of hyponatremia.

12. A method according to claim 9 for the treatment of edematous states.

13. A method according to claim 10 for the treatment of hyponatremia.

14. A method according to claim 10 for the treatment of edematous states.

* * * * *